United States Patent
Cantaluppi et al.

(10) Patent No.: US 9,061,018 B2
(45) Date of Patent: Jun. 23, 2015

(54) USE OF MICROVESICLES (MVS) DERIVED FROM STEM CELLS FOR PREPARING A MEDICAMENT FOR ENDO/EPITHELIAL REGENERATION OF DAMAGED OR INJURED TISSUES OR ORGANS, AND RELATED TO IN VITRO OR IN VIVO METHODS

(71) Applicant: Fresenius Medical Care Deutschland GmbH, Bad Homburg, DE (US)

(72) Inventors: Vincenzo Cantaluppi, Tavernerio (IT); Maria Deregibus, Torino (IT); Giovanni Camussi, Torino (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 14/027,383

(22) Filed: Dec. 2, 2013

(65) Prior Publication Data
US 2014/0134264 A1 May 15, 2014

Related U.S. Application Data

(62) Division of application No. 12/734,396, filed as application No. PCT/IT2007/000753 on Oct. 29, 2007, now Pat. No. 8,568,771.

(51) Int. Cl.
A61K 35/44 (2006.01)
A61K 35/28 (2006.01)
A61K 35/22 (2015.01)
A61K 35/407 (2015.01)

(52) U.S. Cl.
CPC .................. *A61K 35/44* (2013.01); *A61K 35/22* (2013.01); *A61K 35/28* (2013.01); *A61K 35/407* (2013.01)

(58) Field of Classification Search
CPC .................................................... A61K 35/44
See application file for complete search history.

(56) References Cited

FOREIGN PATENT DOCUMENTS

WO   WO 2005/121369   12/2005
WO   WO 2006/077410   7/2006

OTHER PUBLICATIONS

Deregibus et al (Blood. Published online May 29, 2007; 110: 1440-1448).*
Romanov et al. (Canadian Journal of Pharmacology. 2007; 85: 396-403).*
Ratajczak et al. Leukemia, 2006; 20: 847-856.
Jang et al. Nature Cell Biology. Jun. 2004; 6(6): 533-539.
Deregibus et al. Blood. May 29, 2007; 110: 1440-1448.
Basile, International Society of Nephrology. May 2, 2007; 72: 151-157.
Bonventre et al. Recent Advances in the Pathophysiology of Ischemic Acute Renal Failure, J.Am.Soc.Nephrol 14: 2199-2210, 2003.
Bonventre et al. Dedifferentiation and Proliferation of Surviving Epithelial Cells in Acute Renal Failure, J.Am.Soc.Nephrol 14: S55-S61, 2003.
Iruela-Arispe et al. Participation of Glomerular Endothelial Cells in the Capillary Repair of Glomerulonephritis, Am.J. Pathol., v. 147, n.6, Dec. 1995, 1715-1727.
Herrera et al. Exogenous mesenchymal stem cells localize to the kidney by means of CD44 following acute tubular injury, Kidney Int. 2007, 72, 430-441.
Biancone et al. Role of L-Selectin in the Vascular Homing of Peripheral Blood-Derived Endothelial Progenitor Cells, J.Immunol. 2004; 173; 5268-5274.
Kunter et al. Mesenchymal Stem Cells Prevent Progressive Experimental Renal Failure but Maldifferentiate into Glomerular Adipocytes, J.Am.Soc.Nephrol. 18: 1754-1764; 2007.
Chertow et al. Mortality after acute renal failure: Models for prognostic stratification and risk adjustment, Kidney Int. 2006; 70; 1120-1126.
Mehta et al. Spectrum of acute renal failure in the intensive care unit: The PICARD experience, Kidney Int. 2004; v. 66; 1613-1621.
Bonegio et al. Role of apoptosis in the pathogenesis of acute renal failure, Curr.Opin.Nephrol Hypertens 2002; 11:301-308.
Tonelli et al. Acute Renal Failure in the Intensive Care Unit: A Systematic Review of the Impact of Dialytic Modality . . . , AmJ. Kidney Dis. 2002; v. 40, n. 5, 875-885.
Bussolati et al. Isolation of Renal Progenitor Cells from Adult Human Kidney, AmJ.Pathol. 2005; v. 166, n. 2, 545-555.

* cited by examiner

*Primary Examiner* — Scott Long
(74) *Attorney, Agent, or Firm* — Jacobson Holman, PLLC.

(57) ABSTRACT

The invention relates to the use of microvesicles (MVs) derived from stem cells for preparing a medicament for the endo/epithelial regeneration of damaged tissues or organs and/or for inhibiting the apoptosis induced by cytostatic agents. The stem cell from which the microvesicles are obtained is preferably selected from the group consisting of endothelial progenitor cells (EPCs), mesenchimal stem cells (MSCs), renal progenitors CD133+, adult human liver stem cells (HLSC) and any combination thereof. The microvesicles may be used in both in vitro and in vivo applications, such as for example the regeneration of damaged tissues or organs and the treatment of renal injury and hepatic injury, particularly acute renal failure (ARF) and acute hepatic failure (AHF).

7 Claims, 10 Drawing Sheets

USE OF MICROVESICLES (MVS) DERIVED FROM STEM CELLS FOR PREPARING A MEDICAMENT FOR ENDO/EPITHELIAL REGENERATION OF DAMAGED OR INJURED TISSUES OR ORGANS, AND RELATED TO IN VITRO OR IN VIVO METHODS

The present invention generally fills within the field of tissue regeneration, and in particular it relates to endothelial and epithelial regeneration.

In complex organs, the cross-talk between the endothelial and epithelial compartments is relevant in differentiation, function and repair. After injury the morphologic repair and functional recovery depend on the regeneration of both endothelial and epithelial cells, thus restoring cell-to-cell interaction.

Endothelial cells originate from the ectodermic germ layer and represent the first interphase between blood and the vascular wall. They represent 1% of the whole body mass, with a surface of about 28 $m^2$ for arteries and 280 $m^2$ in capillaries. The vascular endothelium is known to have a wide range of biological activities such as secretion of mediators, sensing of the mechanical stress, vasoregulation, neuro-humoral control and regulation of inflammatory cell adhesion and extravasation.

Epithelial cells originate from the endodermic germ layer and are largely represented in the majority of organs, wherein they have acquired specific functions. In the kidney, epithelial cells have differentiated into specific structures (proximal and distal tubular cells with the specialized function of re-absorption and secretion of pre-urine and glomerular epithelial cells with the specialized function of regulating selective permeability) In the liver, the epithelial cells mainly constitute the anatomic functional unit of the hepatic lobule. This structure is specialized in the production of bilirubin and biliary salts which are among others specific neo-synthetic products. In the pancreas, several types of epithelial cells are specialized in the secretion and handling of different hormones (i.e. beta-cells for insulin secretion).

The epithelial and endothelial cells are targets for several injurious mechanisms that may lead to acute or chronic organ dysfunction. The repair process at the organ level depends on the ability of the endothelial and epithelial cells to de-differentiate, proliferate and finally migrate at the site of injury and eventually re-differentiate, thus insuring the complete morphologic and functional recovery. For instance, following an acute tubular necrosis, which is a clinically relevant event subsequent to ischemic or toxic events, the reparative events require proliferation and final differentiation into mature cells of both cell types (1,2). In renal glomerular diseases the recovery from injury is essentially related to the vascular remodelling of the structures of the glomerulus. More in detail, the neoangiogenesis occurring during the regenerative phase of glomerular disease has been shown to affect also the functional recovery of podocytes, a highly differentiated epithelial cells regulating the glomerular selective permeability (3). In many models of acute vascular injury the regeneration of endothelial cells is instrumental to the restoration of the tissue and organ functions which is also associate to the repair of the epithelial functional component of the organ. Bone marrow-derived mesenchymal stem cells and endothelial progenitor cells (EPCs) are preferentially recruited to sites of vascular ischemia through adhesion molecule signals (4, 5).

To date, the existing approaches to treat the endo/epithelial damage or injury have been based on the use of 1) growth factors acting on both or one of the two cell types; 2) cell therapy using mesenchymal stem cells or EPC. However, the existing approaches have a number of drawbacks.

The use of growth factors has the disadvantage of high costs of production and the need to obtain biological effects of an appropriate combination of different growth factors. The use of stem cell therapy has intrinsic risks given the loss of control on the administered cells once they have been implanted in the recipient with potential tumorigenic risk or inappropriate differentiation. For instance, adipogenic differentiation within injured glomeruli has been reported in an experimental model of glomerulonephritis (6).

The present inventors have now found that microvesicles (MVs) derived from stem cells represent an advantageous alternative over the existing approaches for the treatment of endo/epithelial damage or injury, in that their use does not entail the above mentioned drawbacks. Furthermore, the fact that microvesicels derived from stem cells have the ability of regenerating both endothelial and epithelial tissue damage or injury is quite unexpected. Actually, it was known in the prior art (7) that microvesicles derived from endothelial progenitor cells (EPCs) are capable of promoting angiogenesis and capillary-like structures formation from endothelial cells. It was also known e.g. from WO2005121369 that a microvesicle from a donor cell or a synthetic microvesicle can be employed to modify a cell that is contacted with the microvesicle. Typically, the modification is at least in part effected by RNA of the microvesicle, but it may also be effected by a lipid component of the microvesicle, a membrane associated peptide of the microvesicle, or a cytosolic peptide of the microvesicle.

However, the combined ability of microvesicles derived from a number of types of stem cells, including EPCs, of promoting the regeneration of both endothelial and epithelial tissue had never been disclosed nor suggested.

Figure 1:
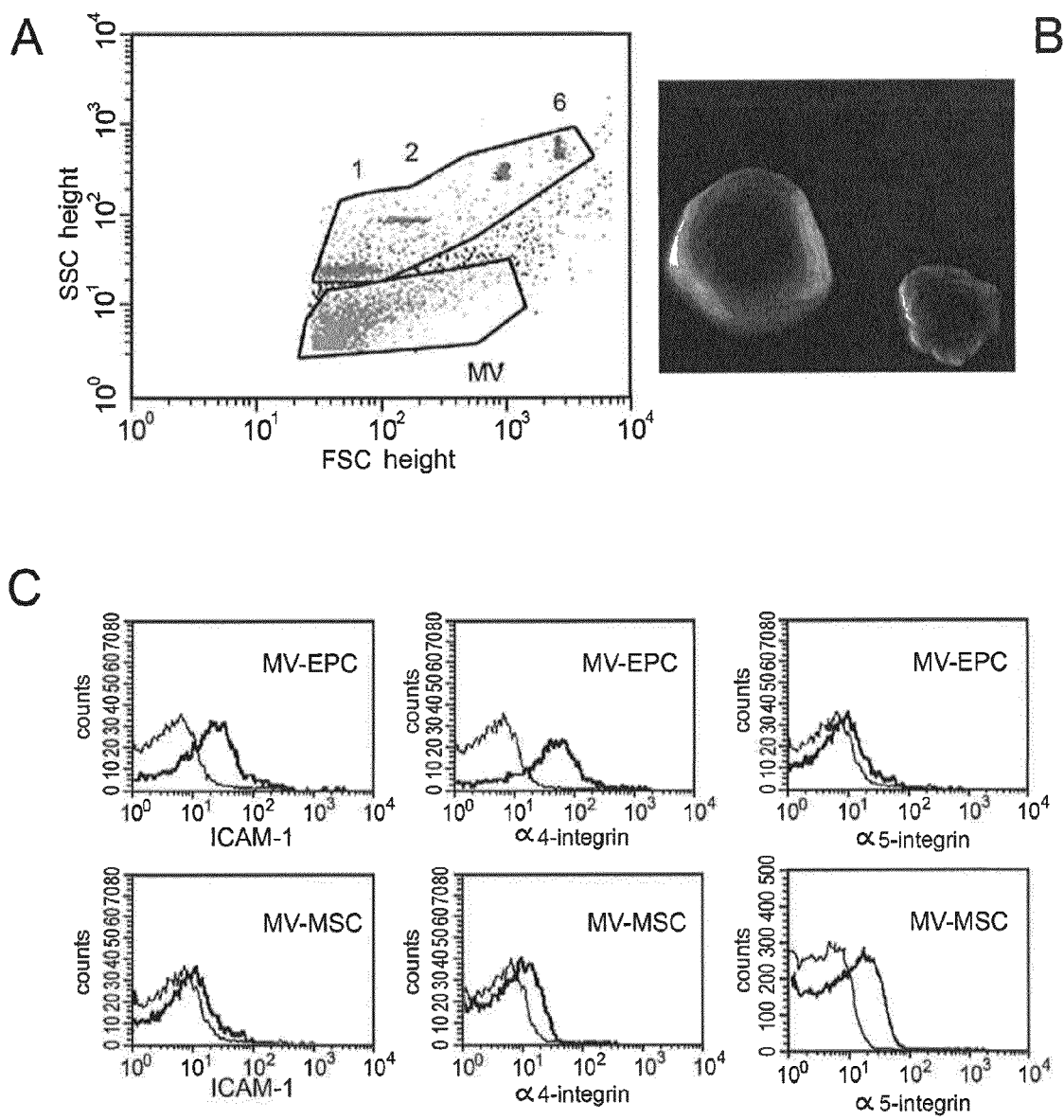
FIG. 1A graphically represents the results of FACS analysis with 1, 2, 4 and 6 μm beads as the size internal standards for MVS derived from human EPC, MSC and CD133-renal progenitors FIG. 1B graphically represents the results of scanning and transmission electron microscopy showing the spheroid morphology of MVS.
FIG. 1C graphically represents the results of FACS analysis of MVS.

Thanks to their regeneration abilities, the stem cell-derived MVs used in the invention may be employed in tissue repair, particularly for endolepithelial regeneration after tissue damage or injury. The MVs employed within the invention may be used for both in vitro and in vivo applications.

As to the in vivo applications, the stem cell-derived MVs have been shown to share a number of common biological effects, which render them particularly suitable for use as a medicament in human applications for renal and hepatic repair, particularly for the treatment of acute renal failure (ARF) and acute hepatic failure (AHF). Actually, the MVs employed in the invention have been shown to be effective in the recovery from acute tubular injury, the recovery from acute glomerulonephritis, and in promoting glomerular capillaries regeneration and hepatocyte proliferation, thereby being of great benefit in the treatment of ARF and AHF.

The ability of the kidney to recover following episodes of acute injury has a critical impact on patient morbidity and mortality in the hospital setting (8, 9). The renal tubular cells are particularly susceptible to injury when exposed to endogenous cytokines such as in sepsis, to endogenous or exogenous toxins such as myoglobin or aminoglycosides and radiocontrast agents, or to episodes of renal ischemia (10). Recovery from acute kidney injury depends on the ability of renal tubules to regenerate and regain normal function (2). The age of the patient and the severity of injury may condition the recovery. After severe or repeated episodes of renal injury, the recovery can be impaired or even fail leading to the requirement for long-term dialysis and to an increase in patient mortality (11). Necrosis and loss of tubular epithelial cells is the most common event in acute renal failure (ARF) and the recovery of renal function following acute renal failure is dependent on the replacement of necrotic tubular cells with functional tubular epithelium (2). The absence or reduction of epithelial and endothelial regeneration may predispose to tubulo-interstitial scarring and chronic renal disease. Studies on the physiological response to renal injury indicate that tubular cells, after the insult had occurred, dedifferentiate and acquire a mesenchymal phenotype. Dedifferentiated cells then migrate into the regions where tubular cells underwent necrosis, apoptosis or detachment with denudation of the tubular basement membrane. This process is followed by cell proliferation and eventually by their subsequent differentiation into functional epithelial cells with restoration of tissue integrity (2). It has been also suggested that the interstitium of the kidney contains adult renal stem cells capable to contribute to renal repair (12). Glomerular injury is frequently followed by progression to sclerotic lesions as glomerular cells have a limited regeneration in respect to tubuli. The loss of capillaries is a common event in several different glomerular diseases that progress to an end stage renal failure (13).

One aspect of the present invention is therefore the use of a stem cell-derived microvesicle for preparing a medicament for endo/epithelial regeneration.

In a preferred embodiment, the medicament is directed to the treatment of renal injury, such as acute renal failure (ARF).

In another preferred embodiment, the medicament is directed to the treatment of hepatic injury, such as acute hepatic failure (AHF).

Given the ability of the stem cell-derived microvesicles (MV) to inhibit apoptosis and promote cell proliferation, such MVs are also particularly suitable for use in the inhibition of apoptosis induced by cytostatic agents, thereby reducing the side effects of chemotherapy of cancer.

Thus, another aspect of the invention is the use of a stem cell-derived microvesicle for preparing a medicament for the inhibition of apoptosis induced by a cytostatic agent.

Cytostatic agents are for example Paclitaxel, Lenalidomide, Pomalidomide, Epirubicin, 5FU, Sunitinib, Lapatinib, Canertinib, cyclophosphamide, doxorubicin, Lenalidomiden/Dexamethason, Pomalidomide/Dexamethasone, Carboplatin, mitoxantron, oxaliplatin, docetaxel, vinorelbin.

The medicament of the invention is suitably administered by intravenous infusion and it may be prepared in a dosage form suitable for the administration of an amount of microvesicles comprised between about 30 to 120 μg/kg body weight of the recipient. The recipient is any patient in need of a treatment capable of effecting endo/epithelial regeneration, such as for example a human affected by ARF or AHF.

The expression "microvesicle (MV) derived from a stem cell" as used herein refers to a membrane particle which is at least in part derived from a stem cell. In turn, the term "stem cell" includes any undifferentiated or partially undifferentiated cell which is capable of proliferating (self-renewal) and differentiating (palsticity), thereby replacing the mature cells of a specialized cell lineages which have reached the end of their life cycle. The term "stem cell" as used in the present description includes both stem cells having unlimited self-renewal ability and pluripotent plasticity, and progenitor cells with multipotent or unipotent plasticity and, in some instances, a limited self-renewal ability.

In a preferred embodiment of the invention, the stem cell-derived MVs used in the invention are derived from stem cells selected from the group consisting of endothelial progenitor cells (EPCs), mesenchymal stem cells (MSCs), renal progenitors CD133+, adult human liver stem cells (HLSC).

The microvesicles derived from stem cells used in the present invention are generally spheroid in shape and have a diameter within the range of 100 nm to 5 μm, more typically of between 0.2 and 1 μm. If the particle is not spheroid in shape, the above-mentioned values are referred to the largest dimension of the particle.

The stem cells from which the microvesicles used in the invention are obtained may be isolated as described in the experimental section of the description. The microvesicles (MVs) may then be obtained from the supernatants of the isolated stem cells, by ultracentrifugation as disclosed in the experimental section of the description.

The isolated MVs may then be stored until use by freezing at very low temperature, typically at −80° C., in a suspension with one or more cryoprotecting agents. Suitable cryoprotecting substances are for example dimethylsulphoxide (DMSO) and glycerol. The use of DMSO at a concentration of 1% of the cell suspension volume guarantees good preservation of the cells and a limited toxic effect on reinfused patients. Other substances which may be cited are extracellular cryoprotecting agents, that is to say high molecular weight substances acting at the cell surface forming a tight barrier which reduces intracellular dehydration. Hydroxyethylic starch may be cited as an example. The isolated MVs may then be used for the preparation of the medicament.

The isolated stem cell-derived MVs were tested by the present inventors both in vitro and in vivo. The experimentation carried out in vivo included a murine toxic ARF model and an experimental model of rat glomerulonephritis induced by intravenous injection of anti-Thy-1 antibody.

The following experimental section is provided by way of illustration only.

Materials and Methods

Cell Preparations

Isolation and Characterization of Endothelial Progenitor Cells (EPCs), Mesenchymal Stem Cells (MSCs) and CD133 Renal Progenitor Cells EPC were isolated from peripheral blood mononuclear cells from healthy donors by density centrifugation and plated on fibronectin-coated culture flasks in endothelial cell basal medium-2 (Clonetics, Biowhittaker, Walkersville, Md.) supplemented with 5% FBS, VEGF, FGF-2, EGF, and insulin-like growth factor-1. Endothelial identity was studied by FACS, Western Blot, gene-micro array analysis, and functional evaluation of angiogenic properties on Matrigel-coated plates as previously described (5). Human mesenchymal stem cells (hMSCs) were isolated and cultured as previously described (4). Murine MSCs (mMSCs) from femurs and tibias of 8-wk-old mice were obtained as previously described (14). Cells were plated at a density of $20\text{-}40\times10^6$ cells per 9.5 cm$^2$ in α-MEM (Invitrogen, Paisley, Scotland), supplemented with 10% FCS, 10% horse serum (both form Euroclone, Wetherby, UK), 2 mM L-glutamine, 100 µg/ml streptomycin, and 100 IU/mL penicillin (all from Sigma, St Louis, Mo., USA). The no adherent cell population was removed after 72 h and the adherent layer washed once with fresh media. Cells had a typical spindle-shaped appearance, and the MSC phenotype was confirmed by expression of mesenchymal stem cell markers and by ability to differentiate into osteocytes and adipocytes, as described (14). Renal progenitor cells were obtained from normal portion of cortex obtained from surgically removed kidneys. After dissection and passage through a graded series of meshes, CD133$^+$ cells were isolated from the tubular fraction by magnetic cell sorting, using the MACS system (Miltenyi Biotec, Auburn, Calif.). CD133$^+$ cells were plated onto fibronectin in the presence of 60% DMEM LG (Invitrogen, Paisly, United Kingdom), 40% MCDB-201, with 1× Insulin-transferrin-selenium, 1× linoleic acid 2-phosphate, $10^{-9}$ M dexametasone, $10^{-4}$ ascorbic acid 2-phosphate, 100 U penicillin, 1,000 U streptomycin, 10 ng/ml EGF and 10 ng/ml PDGF-BB (all from Sigma-Aldrich, St. Louis, Mo.) and 2% FCS (Euro-Clone, Wetherby, United Kingdom) (12). Selected cells lacked the expression of haematopoietic markers, and expressed PAX-2, an embryonic renal marker, suggesting their renal origin. Renal tissue-derived CD133$^+$ cells and clones of individual cells were capable of expansion and limited self-renewal and differentiated in vitro into epithelial or endothelial cells. In vitro epithelial differentiation was obtained in the presence of FGF-4 (10 ng/ml) and HGF (20 ng/ml) (Sigma). Endothelial differentiation was obtained culturing the cells in EBM medium (Cambrex Bio Science, Baltimore, Md.) with VEGF (10 ng/ml) (Sigma) and 10% FCS on Endothelial Cell Attachment Factor (Sigma) (12). Upon subcutaneous implantation in SCID mice, the undifferentiated cells formed tubular structures expressing renal epithelial markers.

Isolation and Characterization of MVs from Stem Cells

MVs were obtained from supernatants of different progenitor cell cultures cultured in medium deprived of FCS (7). After centrifugation at 2,000 g for 20 minutes to remove debris, cell-free supernatants were centrifuged at 100,000 g (Beckman Coulter Optima L-90K ultracentrifuge) for one hour at 4° C., washed in serum free medium and submitted to a second ultracentrifugation in the same conditions. Endotoxin contamination was excluded by Limulus test according to the manufacturer's instruction (Charles River Laboratories, Wilmington, Mass.). The MVs obtained were analyzed by as follows:

FACS Analysis:

the size of MVs was determined by FACS (Becton Dickinson). Beads of different sizes (1, 2, 3, 4, 6, 10 and 15 µm, Molecular Probes, Invitrogen) were used as the size markers and analysis was performed using a log scale for FSC and SSC parameters.

Scanning and Transmission Electron Microscopy:

MVs were fixed in Karnowski fixative, dehydrated in alcohol, dried on glass surface and coated with gold by sputter coating. The specimens were examined in a scanning Jeol T300 electron microscope. Images were obtained via secondary electron at a working distance of 15-25 mm and at an accelerating voltage of 20-25 kV. Transmission electron microscopy was performed on Karnovsky's-fixed, osmium tetraoxide-postfixed tissues and embedded in epoxy resin according to standard procedures. Ultra-thin sections were stained with uranil acetate and lead citrate and were examined with a Jeol JEM 1010 electron microscope.

Gene Array Analysis:

Human GEarray kit for the study of apoptosis (GEArray Q series Human Apoptosis, SuperArray Inc., Bethesda, Md.) was used to characterize the gene expression in tubular cells treated with MVs. RNA pooled from different experiments was used as a template for biotinylated probe synthesis. Gene expression was detected by chemiluminescence signal using the alkaline phosphatase substrate, CDP-Star and directly acquired according to Manufacturer's. Densitometric analysis was performed using the Quantity one program (Life Science) and row data analyzed with the GEArray analyzer program analysis.

In Vivo Models

Marine Toxic ARF Model

Acute toxic tubular injury in C57Bl/6 mice was induced by intramuscular injection of 7.5 ml/kg body weight of 50% glycerol solution (Sigma, St. Louis, Mo.), as previously described (14). Renal function was assessed by determination of serum creatinine and urea levels (Beckman Instruments Inc., Fullerton, Calif.). The peak of tubular injury occurred 3 days after glycerol injection (14). Mice were sacrificed after 3, 6, 10 and 15 days from ARF induction, in order to evaluate the phases of maximal injury and of tubular regeneration. Kidneys were formalin-fixed and paraffin-embedded for histology and immunohistochemistry analysis.

Experimental Model of Thy-1 Glomerulonephritis

Glomerulonephritis (GN) was induced by intravenous administration at day 0 of 250 µg/100 g weight of anti-Thy1-1 antibody (Ab) into femoral vein of 6-wk-old female Lewis rats. Control animals received the same volume of saline injection instead of anti-Thy1.1 Ab. At day 2, when proteinuria was already detectable, 30 µg of EPC-derived MVs were injected in the controlateral femoral vein. Control animals received injection of the same amount of vehicle alone (M199 medium Hepes modified plus 1% DMSO). Proteinuria, serum and urine creatinine/urea (24 hour urine collection) were evaluated daily. Mice were sacrificed at the following days D4, D7, D14. Each experimental group included 9 rats.

In Vitro Experiments

Human, Tubular Cell Isolation and Culture

Primary cultures of human TEC (PTEC) were obtained from kidneys removed by surgical procedures from patients affected by renal carcinomas (15). An immortalized cell line of PTEC generated by infection with a hybrid Adeno5/SV40 virus was used to confirm and to extend the experiments carried out with primary tubular cells. Cells were grown with RPMI 1640 (GIBCO, Grand Island, N.Y.) containing 10% FCS (Hyclone, Logan, Utah) and 2 mM glutamine (GIBCO).

Cell Proliferation Assay

Cells were seeded at 8000 cells/well into 96-well plates in DMEM medium containing 10% FCS and left to adhere. DNA synthesis was detected as incorporation of 5-bromo-2-deoxyuridine (BrdU) into the cellular DNA using an ELISA kit (Roche Applied Science). Briefly, cells were added with 10 μM BrdU, incubated in DMEM with or without 10% FCS for 18 h. Cells were then fixed with 0.5 M ethanol/HCl and incubated with nuclease to digest the DNA. BrdU incorporated into the DNA was detected using an anti-BrdU peroxidase-conjugated mAb and visualized with a soluble chromogenic substrate. Optical density was measured with an ELISA reader at 405 nm.

Apoptosis Assays

Apoptosis was evaluated using the TUNEL assay analysis (ApopTag Oncor, Gaithersburg, Md.). After different pro-apoptotic stimuli, cells were suspended in PBS, fixed in 1% para formaldehyde in PBS pH 7.4 for 15 minutes at 4° C., washed twice in PBS and then post-fixed in pre-cooled ethanol-acetic acid 2:1 for 5 minutes at −20° C. Samples were treated. with terminal deoxynucleotidyl transferase (TdT) enzyme. Cells were then treated with warmed anti-digoxigenin conjugate with fluorescein and incubated for 30 minutes at room temperature. Samples were mounted in medium containing 1 μg/ml of propidium iodide and the cells analyzed by immunofluorescence. Results are expressed as percentage of green fluorescence emitting cells (apoptotic cells) versus red fluorescence emitting cells (total cells).

Detection of Caspase 3-8-9 Activities

The activity of caspase-3-8-9 was assessed by ELISA (Chemicon, Temecula, Calif.) based on the spectrophotometric detection of the cromophore p-nitroanilide (pNA) after cleavage from the labelled substrate DEVD-pNA, that is recognized by caspases. Tubular lysates were diluted with an appropriate reaction buffer and DEVD-pNA was added at a final concentration of 50M. Samples were then analysed in an automated ELISA reader at a wave length of 405 nm. Each experiment was performed in triplicate.

FACS Analysis

For FACS analysis, cells were detached from tissue culture plates with EDTA, washed twice with 1×PBS and stained for 1 h at 4° C. with primary antibodies directed to different molecules or with an irrelevant control antibody. Cells were incubated with Alexa Fluor-conjugated secondary antibodies for 45 min at 4° C. The cells were fixed in 1% paraformaldehyde and subjected to FACS analysis (Becton Dickinson, Mountain View, Calif.).

Western Blot Analysis

For Western blot analysis, cells were detached with EDTA and lysed with a 50 mM Tris-HCl lysis buffer containing 1% Triton-X-100, 10 μM/ml leupeptin, 10 μM phenylmethylsulfonyl fluoride (PMSF) and 100 U/ml aprotinin. After centrifugation of tubular lysates at 15000×g, protein contents of the supernatants were measured by the Bradford method: 30 μg of protein per lane were subjected to sodium dodecyl sulfate (SDS)-10% polyacrylamide gel electrophoresis (PAGE) and electroblotted onto nitrocellulose membrane filters. Blots were subsequently blocked with 5% nonfat milk in 20 mM Tris-HCl (pH 7.5), 500 mM NaCl, plus 0.1% Tween. Membranes were incubated overnight at 4° C. with antibodies directed to Akt, P-Akt, Bcl-xL (all from Santa Cruz Biotechnology) or Pax-2 at a concentration of 500 ng/ml. After extensive washing with 0.1% Tween, blots were stained for 1 h, RT with HRP-conjugated protein A (200 ng/ml, Amersham, Buckinghamshire, UK), washed again with 0.1% Tween, developed with ECL detection reagents (Amersham) and exposed to X-Omat film (Eastman Kodak, Rochester, N.Y.).

Evaluation of Trans-Epithelial Electrical Resistance (TER)

Trans-epithelial electrical resistance (TER) was used as an indicator of epithelial polarity. Cells were plated in transwells on collagen-coated polycarbonate membranes (Corning Costar Corp., Cambridge, Mass.) and allowed to reach confluence before the addition of different stimuli. An epithelial voltohm meter (EVOM; World Precision Instruments, Inc., Sarasota, Fla.) was used to determine TER values as previously described (12). All measures were performed in triplicate and normalized for the area of the membrane.

Detection of FITC-Conjugated Albumin Uptake

Protein uptake was studied after incubation of tubular cells with 50 mg/ml of FITC-conjugated human albumin at 37° C. for 2 h. After FITC-albumin challenge, cells were extensively washed 3× with ice-cold PBS and analysed by FACS.

Migration and Morphogenesis Assays

Migration was evaluated as the speed at which tubular cells migrated into a wound generated in a confluent monolayer in order to simulate a condition of mechanical stress. Cell motility was observed under a Nikon inverted microscope in an hermetically sealed incubator at 37° C. Migration was analysed after digital saving of different images at 30 min of interval using the Micro-Image analysis system (Casti imaging srl, Venezia, Italy). Cellular migration was evaluated by marking the position of the nucleus of more than 30 cells per field. Speed average was calculated as the ratio of straight-line distance between the starting and ending point of observation divided by the time of observation. In selected experiments and for morphogenesis assay, scattered tubular cells were seeded on plates previously coated with 20 μg/ml fibronectin, type IV collagen or Matrigel.

Subcutaneous Matrigel Implants of PTEC is SCID Mice.

Subcutaneous implantation of PTEC in Matrigel plugs was performed to evaluate the tubulogenic effect of stem cell-derived MVs in vivo. Briefly, Matrigel deprived from growth factors (Becton Dickinson) was maintained at −20° C. until use and thawed at 4° C. overnight immediately before implant. 5000 cells were resuspended in 250 μl of fresh medium without FCS and mixed to 500 μl of Matrigel on ice using cooled pipette tips in presence of different stimuli. All samples were s.c. implanted into the posterior limbs of SCID mice. After 1 week mice were sacrificed and Matrigel plugs were retrieved for examination.

Endothelial-Tubular Sandwich Co-Culture

To examine the effect of HMEC incubated with different stimuli on tubular viability, we applied a co-culture model. HMEC were plated on 24-well plates for 24 h in standard culture conditions. HMEC were then subjected to serum deprivation for 24 or 48 hrs in presence or absence of 10 μg/ml of EPC-derived MVs. After incubation under the above mentioned conditions, medium was aspirated, attached cells were extensively washed by 1× PBS and 200 ul of growth factor-reduced Matrigel; (BD) diluted 1:1 with RPMI was used as an overlay and was allowed to gel for 30 minutes at 37° C. Thereafter, $1 \times 10^4$ tubular cells were added to each well to complete the sandwich co-culture. Co-cultures were incubated for additional 24 to 48 h in conditions of serum deprivation. At the end of incubations, tubular cells were subjected to XTT-based assay (Sigma) Data are given as averages ±SD of three different experiments.

Immunofluorescence and Immunocytochemistry

Cytofluorimetric analysis was performed using the following antibodies, all FITC or PE conjugated: anti-CD133-1 monoclonal Ab (mAb) (Miltenyi Biotec), anti-CD44 and anti-human HLA Class I mAbs (Sigma), anti-CD31 and anti-CD105 mAbs (Serotec Inc, Oxford, United Kingdom), anti-KDR mAb (R&D System, Minneapolis, Minn.); anti-Muc-18 mAb (Chemicon International, Temecula, Calif.), anti-CD29, -CD33, -CD34, -CD45, -CD73, -CD90, -CD117 mAbs (Becton Dickinson, San Jose, Calif.). Anti-VE cadherin mAb was kindly provided by Guido Tarone (University of Torino). FITC or PE mouse nonimmune isotypic IgG (Dako, Copenhagen, Denmark) were used as control. Indirect immunofluorescence was performed on cells cultured on chamber slides, fixed in 4% paraformaldehyde containing 2% sucrose and, when needed, permeabilized with Hepes-Triton-X 100 Buffer. Immunofluorescence was also performed on human or mouse tissues rapidly frozen in liquid nitrogen, cut in 3-μm sections and fixed in 3.5% paraformaldehyde containing 2% sucrose. The following antibodies were used: anti-Na—Cl co-transporter, anti-aminopeptidase A and anti-alkaline phosphatase polyclonal goat Abs (Santa Cruz Biotechnology, Santa Cruz, Calif.), rabbit anti-zonula occludens (ZO)-1 polyclonal Ab (Santa Cruz Biotechnology), goat anti-VWF and rabbit anti-Pan-Cytokeratin Abs (Sigma), anti-vimentin and anti-E cadherin mAbs (Dako), anti-EMA mAb (Chemicon International), polyclonal rabbit anti-PAX2 Ab (Covance, Princeton, N.J.) PE-conjugated anti-CD133 (Miltenyi Biotec) and anti-proliferating cell nuclear antigen (PCNA), FITC-conjugated anti-HLA I and anti-calbindin D-28K mAbs (Sigma). Control mouse, rabbit or goat non immune immunoglobulins were used as controls. FITC-conjugated anti mouse, rabbit or goat IgG (Sigma) were used as secondary antibodies, when needed. Immunocyto-chemistry was performed as described (7) on tissue fixed in 10% buffered formalin and embedded in paraffin. Confocal microscopy was performed using a Leika TCS SP2 model confocal microscope (Heidelberg, Germany), Hoechst 33258 dye (Sigma) was added for nuclear staining.

Statistical Analysis

All data of different experimental procedures are expressed as averages±SD. Statistical analysis was performed by ANOVA with Newmann-Keuls multi-comparison test where appropriated.

Results

Characteristics of MVs

FACS analysis with 1, 2, 4 and 6 μm beads as the size internal standards for MVs derived from human EPC, MSC and CD133-renal progenitors was used to determine their size, and it demonstrated that MVs derived from different population of stem/progenitor cells have similar size. The majority of the MVs observed were below the FSC signal corresponding to 1 μm beads (FIG. 1A). Scanning and transmission electron microscopy showed the spheroid morphology of MVs and confirmed that their size was between 0.2-1 μm (FIG. 1B). Images were obtained via secondary electron at a working distance of 15-25 mm and an accelerating voltage of 20-30 kV. By FACS analysis, MVs showed the expression of adhesion molecules known to be expressed by the plasma membrane of the corresponding stem/progenitor cells (FIG. 1C). EPC, MSC-derived MVs and resident renal $CD133^+$ progenitors shared the expression of CD44, CD29 but differed for the expression of ICAM-1, α4 integrin and α5 integrin. These results indicate that the MVs express on their surface several determinants of plasmamembranes of cells from which they originated. The expression of adhesion molecules has been previously shown to be instrumental in the incorporation of MVs in target cells.

In Vitro Biological Effect of MVS on Renal Cells

Tubular injury is a hallmark of Acute Renal Failure (ARF) of ischemic or toxic origin. Moreover, the damage of endothelial cells of peritubular capillaries has been shown to contribute to the extension of kidney damage after ischemia (16). We therefore investigated the effects of MVs released from stem cells on a proximal tubular epithelial cell line (PTEC).

Figure 2:
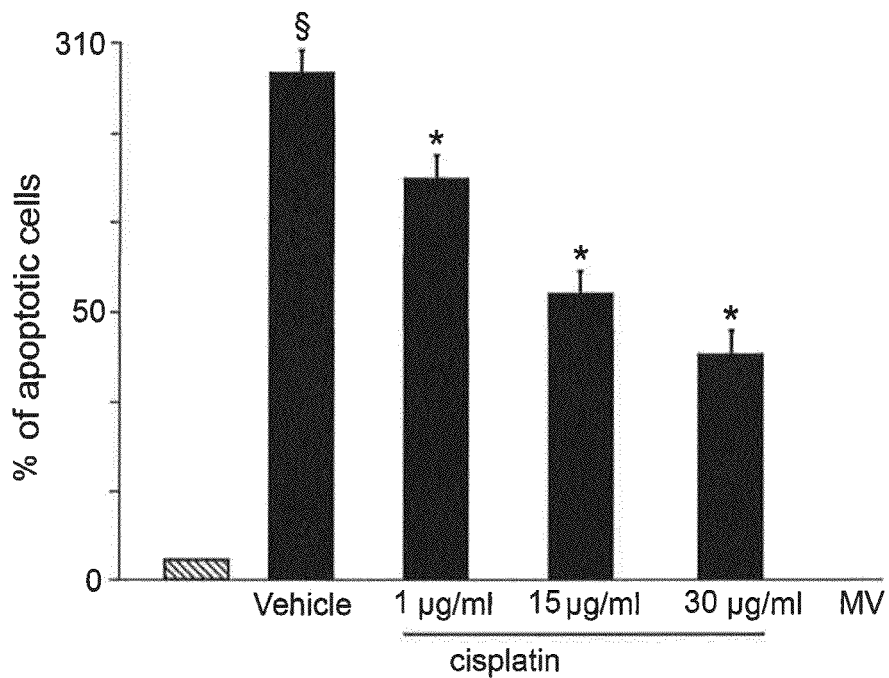
FIG. 2 graphically represents the results of the incubation of MVS with RNase.

MVs Derived from Murine Mesenchymal Stem Cells (mMSCs) Inhibit Apoptosis of PTEC Induced by Cisplatin We found that incubation of PTEC with increasing doses of MVs derived from murine mesenchymal stem cells (mMSCs) significantly reduced apoptosis induced by cisplatin with respect to controls incubated with vehicle alone. The incubation of MVs with RNase abrogated the resistance to apoptosis. The results obtained are shown in FIG. 2. Apoptosis was evaluated by the TUNEL assay as a percentage of apoptotic cells after 24-hours incubation with 0.5 μg/ml cisplatin (dark columns). PTEC were incubated with vehicle alone or with various doses of MVs. Shaded column shows control untreated with cisplatin. Results are expressed as mean±ISD of 3 experiments. Analysis of variance with Dunnet's multi-comparison test was performed: *$p<0.05$ MVs versus vehicle alone.

Expression of PCNA (Proliferating Cell Nuclear Antigen) by PTECs Treated with MVs Indicate Induction of Cell Proliferation MVs derived from mMSC induce the expression of PCNA by PTECs, $5 \times 10^4$ cells/well tubular cells were incubated for 24 hours in DMEM+5% BSA with 10 μg/ml MVs or vehicle alone and the expression of PCNA was evaluated by confocal microscopy. The results obtained showed the absence of nuclear staining for PCNA in PTEC cultured in serum free medium and the nuclear expression of PCNA by PTEC after incubation with MVs derived from mMSC. Three experiments were performed with similar results.

Figure 3:
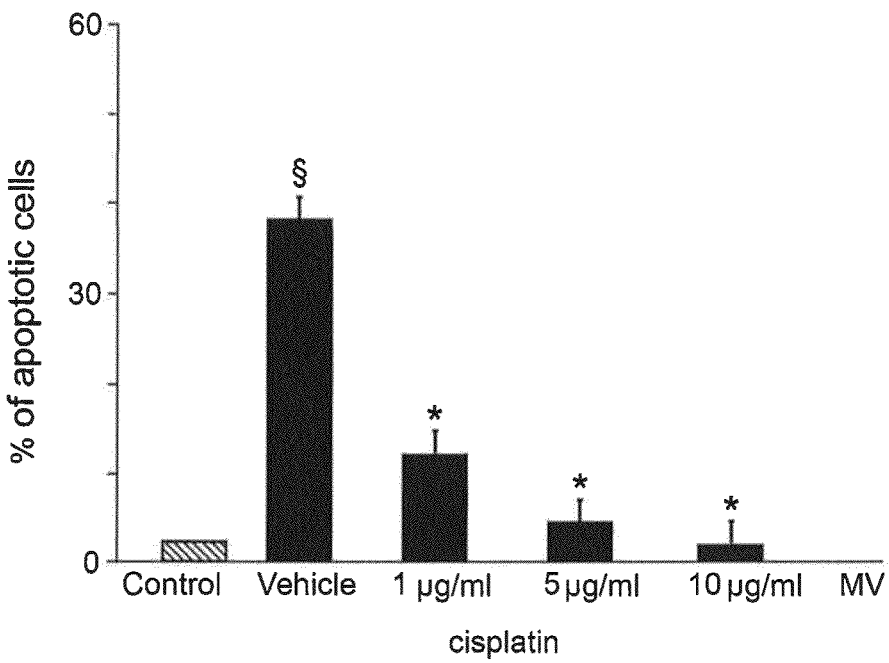
FIG. 3 graphically represents the results of incubation of PTEC with different doses of MVS derived from adult kidney progenitors.

MVs Derived From Human Adult Renal Progenitors CD133+ are Able to Inhibit Apoptosis of PTECs Induced by Cisplatin and to Favour Proliferation of Tubular Epithelial Cells Incubation of PTEC with different doses (1, 5 and 10 μg/ml) of MVs derived from adult kidney progenitors $CD133^+$ significantly inhibited apoptosis induced by cisplatin with respect to controls incubated with vehicle alone (FIG. 3). Apoptosis was evaluated by the TUNEL assay as a percentage of apoptotic cells after 24-hours incubation with 0.5 μg/ml cisplatin (dark columns). Shaded column shows control untreated with cisplatin. The results are expressed as mean±ISD of 3 experiments. Analysis of variance with Dunnet's multicomparison test was performed: *$p<0.05$ MVs versus vehicle alone.

Figure 4:
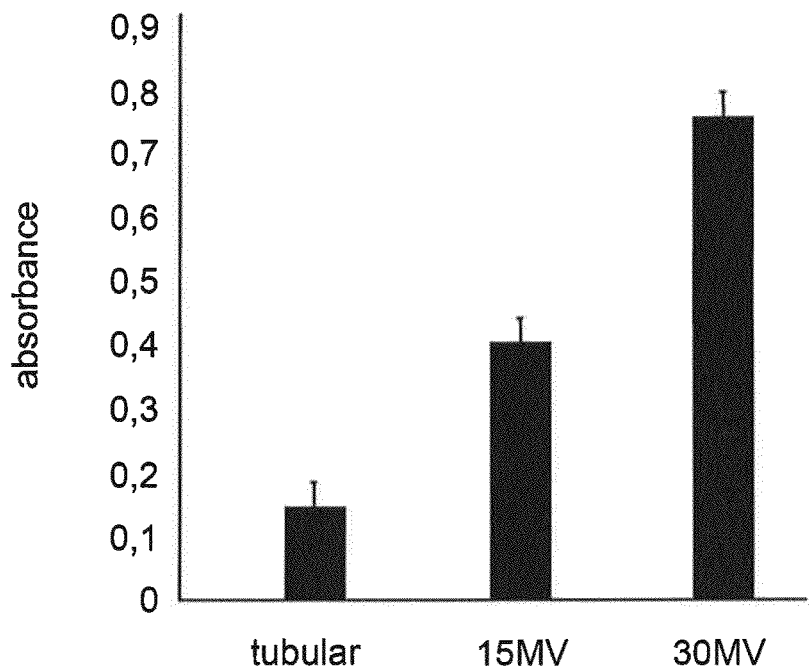
FIG. 4 graphically represents the results of optical density measured with an ELISA reader at 405 nm.

MVs Derived from Human Renal Progenitors $CD133^+$ are Able to Induce Cell Proliferation of PTECs Incubation for 48 hours of PTEC with two different doses of MVs (15 and 30 μg/ml) derived from human kidney progenitors CD133+ significantly promoted cell proliferation of tubular epithelial cells with respect to controls. 8000 cells/well into 96-well plates were added with 10 μM BrdU, incubated in DMEM with vehicle alone or with different doses of MVs. Cells were then fixed with 0.5 M ethanol/HCl and incubated with nuclease to digest the DNA. BrdU incorporated into the DNA was detected using an anti-BrdU peroxidase-conjugated mAb and visualized with a soluble chromogenic substrate. Optical density was measured with an ELISA reader at 405 nm. The results are expressed as mean±ISD of 3 experiments. The results are illustrated in FIG. 4.

Incubation with MVs Induced PAX2 and Vimentin Expression by PTEC After 48 Hours Incubation, Indication a De-Differentiation of PTEC that Acquired an Immature Phenotype MVs derived from human kidney progenitors CD133 induce dedifferentiation of PTECs. $5 \times 10^4$ cells/well PTECs were incubated for 24 hours in DMEM+5% BSA with 10 μg/ml MVs derived from human kidney progenitors CD133 or vehicle alone and the expression of PAX2 and vimentin was evaluated by confocal microscopy.

Figure 5:
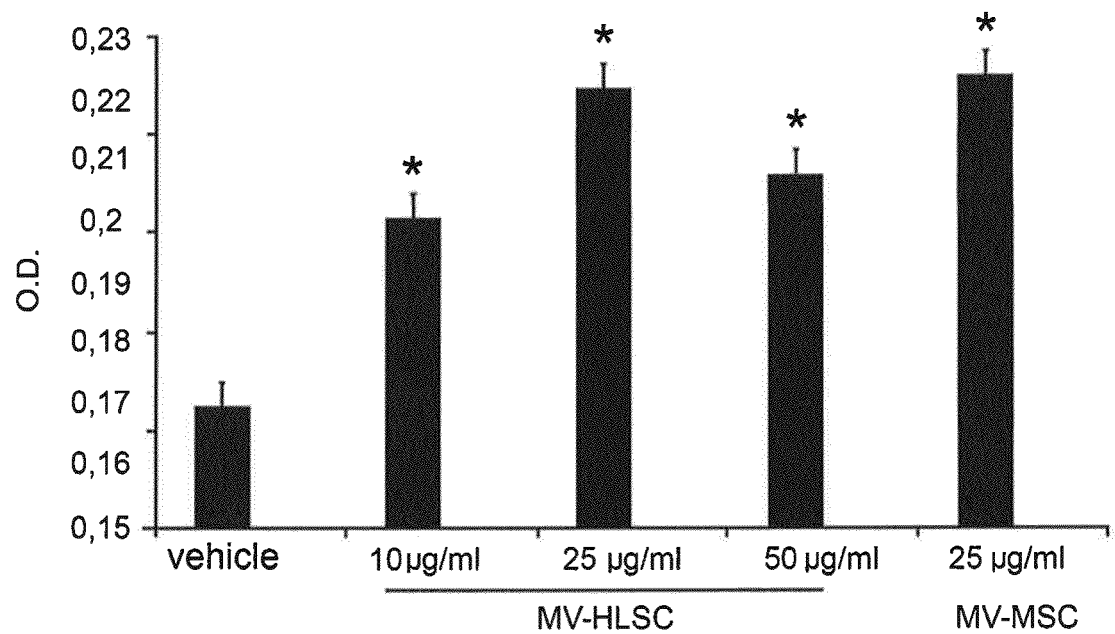
FIG. 5 graphically represents the results of cells incubated in DMEM with a vehicle alone or with different doses of MV.

Cell Proliferation and Apoptosis Assays of Human Hepatocytes Treated with MVs Derived from MSC or HLSC MVs derived from mesenchymal stem cells (MSC) or adult human liver stem cells (HLSC) were able to favour proliferation of human hepatocytes;

Incubation of hepatocytes with different doses (10, 25 and 50 μg/ml) of MV derived from MSC or HLSC for 72 hours promoted cell proliferation in respect to control incubated with vehicle alone. As shown in FIG. 5, 5000 cells/well into 96-well plates were added with 10 μM BrdU, incubated in DMEM with vehicle alone or with different doses of MV. Cells were then fixed with 0.5 M ethanol/HCl and incubated with nuclease to digest the DNA. BrdU incorporated into the DNA was detected using an anti-BrdU peroxidase-conjugated mAb and visualized with a soluble chromogenic substrate. Optical density was measured with an ELISA reader at 405 nm. Results are expressed as mean±ISD of 3 experiments. Analysis of variance with Dunnet's multicomparison test was performed: *$p<0.05$ MV versus vehicle alone. The results clearly show that MVs from MSC and MSC are able to stimulate in vitro proliferation of mature human hepatocytes, suggesting a potential effect on hepatic regeneration.

Apoptosis Assay of Human Tubulae Cells Treated with MVs Derived from HLSC

Apoptosis of human tubular epithelial cells, was evaluated using the TUNEL assay analysis as previously described. Briefly, cells were subjected to terminal deoxynucleotidyl-transferase [TdT]-mediated nick end labelling (TUNEL) assay analysis using cisplatin (2 μg/ml) as a positive control for the induction of apoptosis. Cells were washed in PBS, fixed in 1% paraformaldehyde in PBS, pH 7.4, incubated with TdT enzyme and digoxigenin-dNTP, washed in PBS, and counterstained with anti-digoxigenin-FITC antibody and with propidium iodide (1 μg/ml) in PBS. The FITC-labelled DNA fragments in the apoptotic cells were visualised by inverted UV microscopy. Cells were counted by digital analysis of images obtained using a video camera, positive apoptotic cells were expressed as a percentage of the total cells counted in a 10× inverted microscope field. The concentration of MVs used it this assay was 10, 15, 30 μg/ml for 48 hours.

Figure 6:
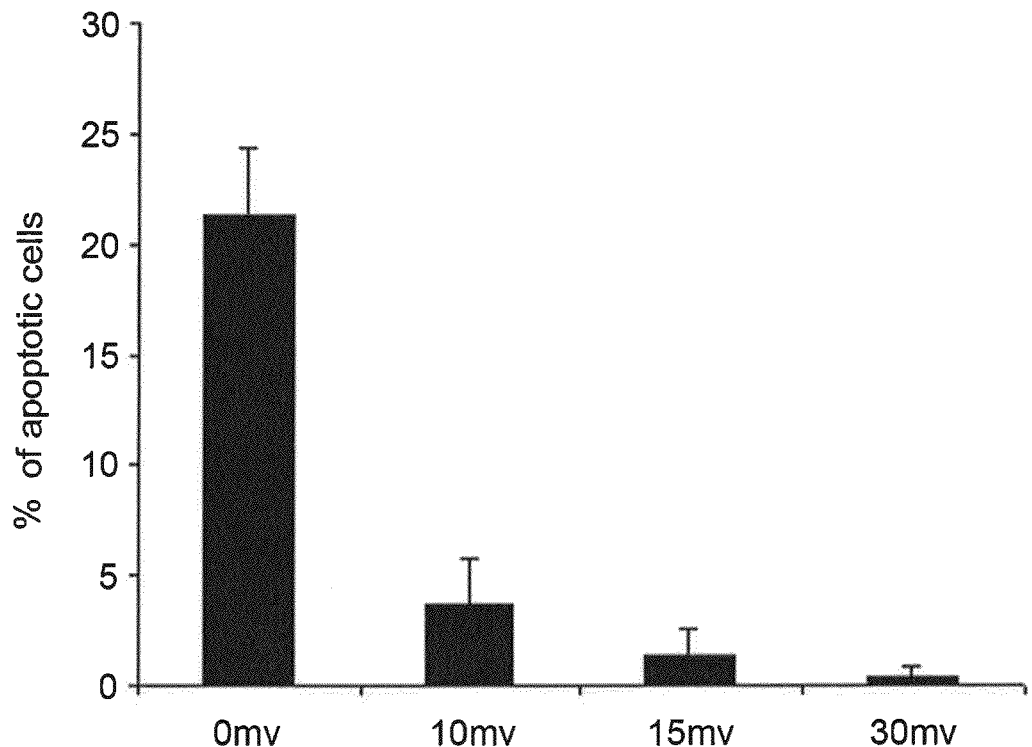
FIG. 6 graphically represents the results (% of apoptosis) of human tubular epithelial cells stimulated with MVS from HLSC.

FIG. 6, shows the % of apoptosis of human tubular epithelial cells stimulated with MVs from HLSC at 10, 15 and 30 μg/ml. The MVs derived from HLSCs stimulated the proliferation of the human tubular epithelial cells which is a primary cell culture, limited to very few passages, in a dose dependent way. The MVs concentrations that stimulated proliferation were: 10, 15, 30 μg/ml. In the case of apoptosis induced by cisplatin, MVs derived from HLSCs inhibit the apoptosis of human tubular epithelial cells at the same concentration that stimulated proliferation.

EPC-Derived MV Exerted a Proliferative and Anti-Apoptotic Effect on PTEC

Figure 7:
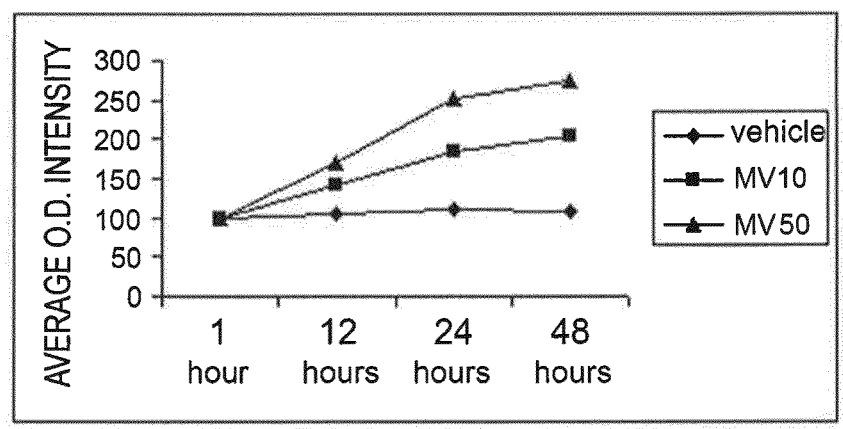
FIG. 7 graphically represents the proliferative effect induced by MVS on PTEC

PTEC were incubated with increasing doses of MVs (1-5 μg/ml)1. MVs induced a proliferative effect after 12 h of incubation with a further increase after 24-48 h in PTEC (FIG. 7). MV-induced proliferation was significantly increased at the dose of 1 μg/ml and reached a peak at the dose of 50 μg/ml (FIG. 7). FIG. 7 shows the proliferative effect induced by MVs on PTEC. Data from XTT-based assay of time-course proliferation of PTEC. MVs induced a significant dose-dependent increase of proliferation at all time points considered (12, 24, 48 hrs). Data are expressed as average±SD of three different experiments. ANOVA with Newman-Keuls multi-comparison test was performed.

Figure 8:
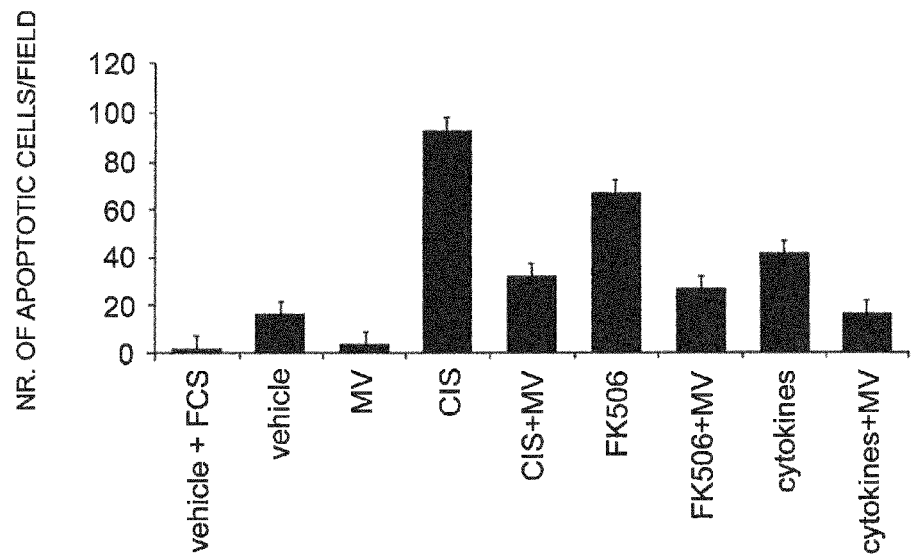
FIG. 8 graphically represents the results of TUNEL assays.

We investigated the anti-apoptotic effect of MVs on PTEC cultured in different detrimental conditions. As shown by TUNEL assay (FIG. 8), MVs significantly reduced apoptosis of PTEC cultured in condition of serum deprivation, with 5 μg/ml cisplatin, 1 μg/ml FK506, or with inflammatory cytokines (20 ng/ml TNF-alpha and 20 ng/ml IFN-gamma). FIG. 8 illustrates the results of the TUNEL assays performed, showing the-anti-apoptotic effect of 10 μg/ml MVs on PTEC exposed to serum deprivation (vehicle/FCS-), cisplatin (CIS 5 μg/ml), FK 506 (1 μg/ml) or inflammatory cytokines (septic: 20 ng/ml TNF-alpha and 20 ng/ml IFN-gamma). Data are expressed as average±SD of three different experiments. ANOVA with Newman-Keuls multi-comparison test was performed.

Figure 9:
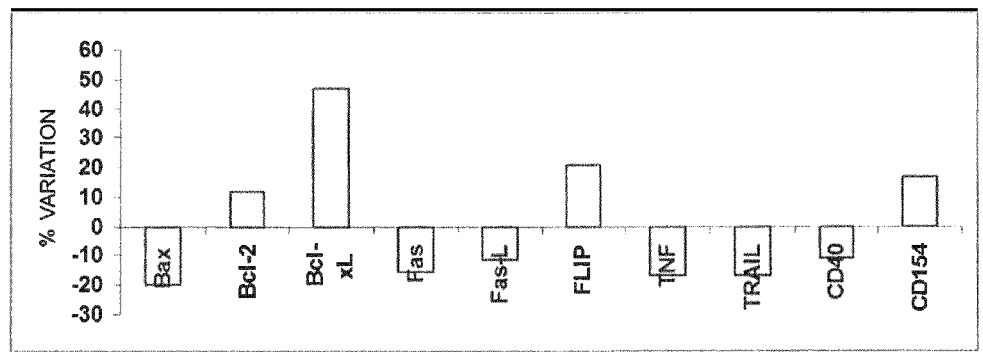
FIG. 9 graphically shows the results of the gene array analysis of PTECs stimulated with cisplatin in the presence or absence of MVS.

The gene array analysis demonstrated that MVs modulated the expression of genes encoding for molecules of the mitochondrial and of the death receptor apoptotic pathways. In particular, MVs induced the up-regulation of anti-apoptotic Bcl-xL, Bcl-2 and FLIP and the down-regulation of several pro-apoptotic genes such as Fas, Fas-ligand (Fas-L), Bax, TNF and TRAIL. In addition, the CD40 gene which is overexpressed in renal tubular epithelial cells during inflammatory injury, was down-regulated, suggesting an anti-inflammatory action of MVs on PTEC. Down-regulation of CD40 was confirmed by FACS analysis. FIG. 9 shows the results of the gene array analysis of PTECs stimulated with cisplatin (5 μg/ml) in presence or absence of 10 μg/ml MVs. Percentage variation of expression of genes involved in apoptosis of PTEC. Results are given as the ratio between densitometric analysis of gene expression in PTEC exposed to cisplatin+MVs with respect to cisplatin alone. House-keeping genes (beta-actin, GAPDH) were used as reference for densitometric analysis. Three experiments were carried out with similar results.

Figure 10:
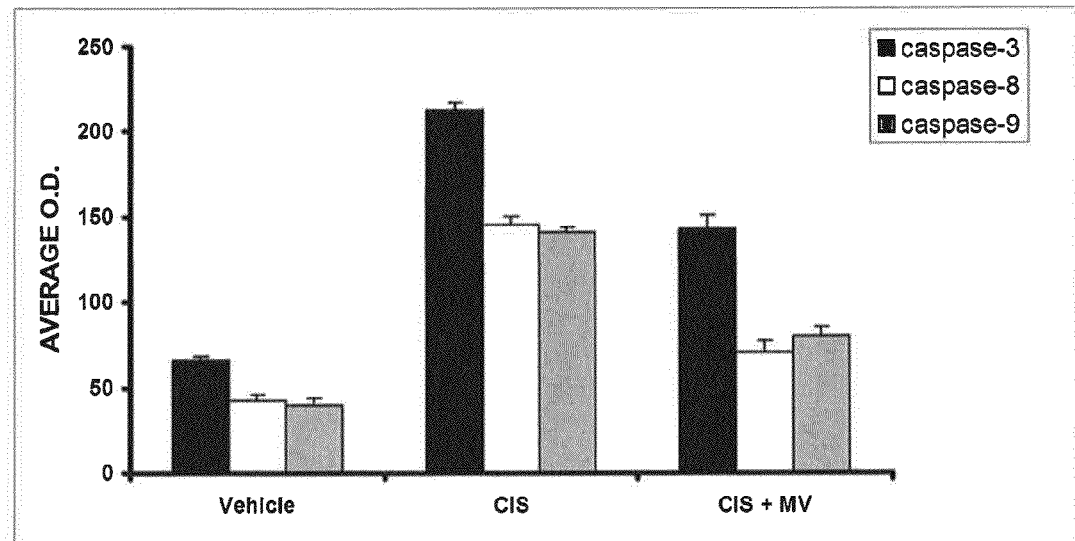
FIG. 10 graphically represents the results of ELISA assays.

Incubation with 10 ng/ml MVs induced a significant reduction of caspase-3-8 and 9 activities in cisplatin-treated iTEC. These results indicated the concomitant inhibition of mitochondrial and receptor-mediated apoptotic pathways. FIG. 10 shows the results of ELISA assays showing the significant reduction in caspase-3, 8 and 9 activities induced by 10 μg/ml MVs on cisplatin-treated PTEC for 24 h. Data are expressed as average±SD of three different experiments. ANOVA with Newman-Keuls multi-comparison test was performed.

Figure 11:
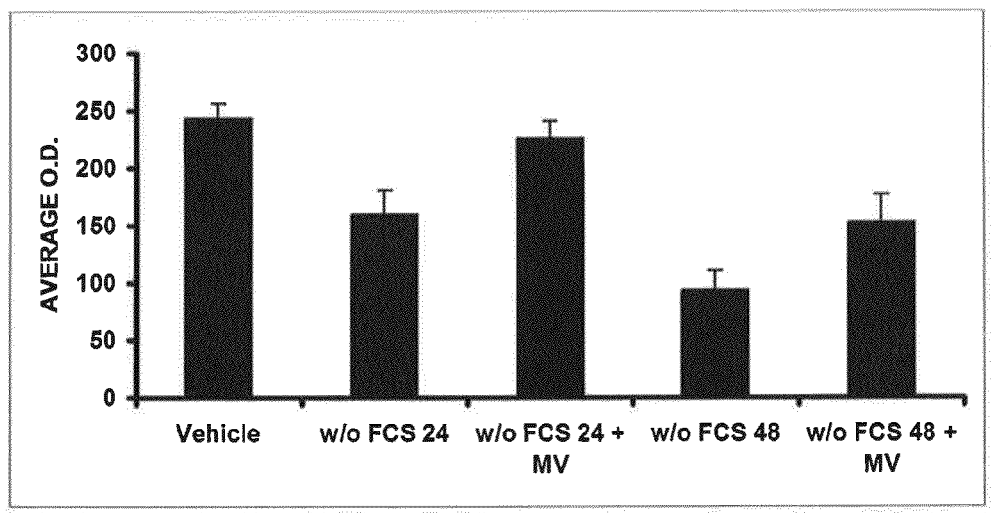
FIG. 11 graphically represents the evaluation of PTEC vitality in an endothelium-PTEC co-culture model.

We evaluated the paracrine effect of endothelial-produced factors on PTEC survival in a model of co-culture characterized by a layer of endothelial cells separated by Matrigel from an upper layer of PTEC. We induced endothelial injury by serum deprivation for 24 or 48 hrs in the presence or absence of 10 µg/ml MVs followed by the stratification of growth factor-reduced Matrigel on which PTEC were seeded. In the absence of MVs, the vitality of PTEC significantly reduce after 24 and 48 h. In contrast, the endothelial stimulation with MVs prevented the decrease of vitality. These results suggest that MVs stimulated a paracrine action of endothelial cells that promotes PTEC survival. The results obtained are illustrated in FIG. 11, concerning the evaluation of PTEC vitality in endothelium-PTEC co-culture model. Endothelial injury was induced by serum deprivation for 24 or 48 h in the presence or absence of 10 µg/ml MVs followed by the stratification of growth factor-reduced Matrigel on which PTEC were seeded. Data are expressed as average±SD of three different experiments. ANOVA with Newman-Keuls multi-comparison test was performed.

We investigated the effect of MVs on the expression of the mesenchymal marker vimentin and of Pax-2, a protein present in embryonic kidneys in human PTEC cultured for 24 h without FCS in presence of 10 µg/ml MVs. MVs induced the expression of vimentin and Pax-2 in PTEC. $5 \times 10^4$ cells/well PTEC were incubated for 24 hours in DMEM+5% BSA with 10 µg/ml MVs derived from EPC and the expression of PAX2 and vimentin was evaluated by confocal microscopy.

MV Induced PTEC Migration

Figure 12:
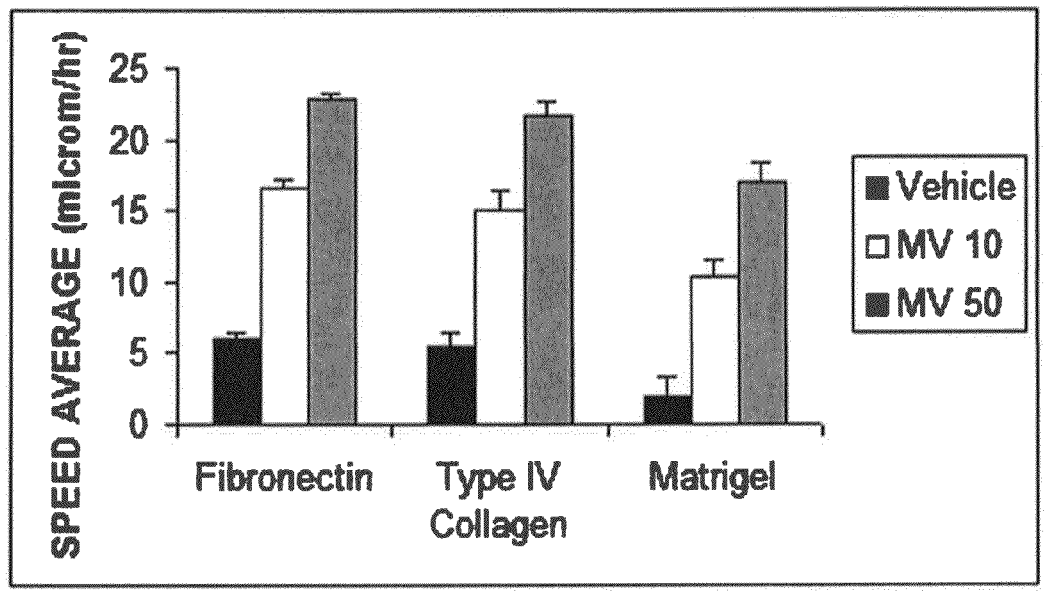
FIG. 12 graphically represents the effect of MVS on migration of PTEC cultured on extra-cellular matrixes.

We evaluated the motility of scattered PTEC seeded on fibronectin-, type IV collagen- or Matrigel-coated plates, a condition mimicking the micro-environment in which PTEC should migrate to re-establish tubular integrity. We studied the effect of MVs on cell migration by time-lapse microscopy on scattered PTEC. The baseline migration rate corresponding to the spontaneous motility of PTEC was found to remain steady for the whole period of observation (12 hours), never exceeding 3-4 µm/hour. MVs induced a significant increase of spontaneous migration that peaked as early as 2 h and remained significantly higher throughout all the observation period on all extracellular matrixes. FIG. 12 shows the effect of MVs on migration of PTEC cultured on extracellular matrixes. Incubation with 10 µg/ml MSP significantly increased the migration of PTEC cultured on plates previously coated with 20 µg/ml human fibronectin, type IV collagen or Matrigel. Data are given as speed average (µm/hr) ±SD of three different experiments.

Figure 13:
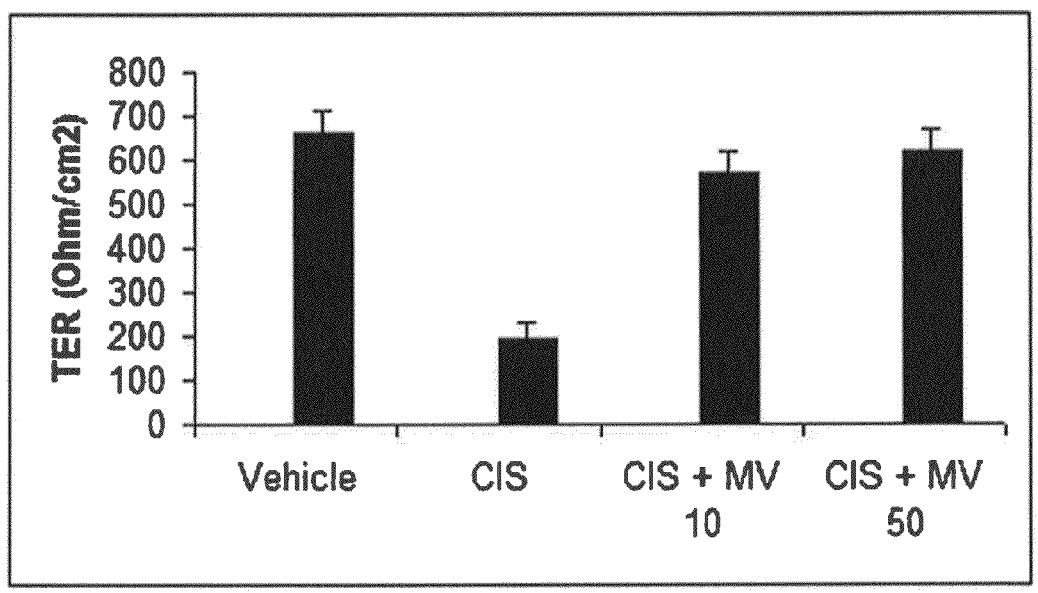
FIG. 13 graphically represents the effect of MVS on cisplatin-induced alteration of trans-epithelial resistance (TER).

MVs Maintain the Functional Integrity of Epithelial Monolayer in Cisplatin-Treated PTEC The addition of MVs to cisplatin-treated PTEC re-established cell polarity, as assessed by trans-epithelial resistance analysis. FIG. 13 shows the effect of MVs on cisplatin-induced alteration of trans-epithelial resistance (TER). Analysis of PTEC TER, a marker of cell polarity, in different experimental conditions: Cisplatin (CIS 5 µg/ml) significantly reduced TER values (*$p<0.05$ CIS vs. vehicle), whereas MVs (10 or 50 µg/ml) restored normal TER values. Data are given as average TER values of three different experiments±SD. TER values were normalized for the area of the membrane used in the experimental procedure. ANOVA with Newman-Keuls multi-comparison test was performed.

Moreover, in the presence of MVs, cisplatin-treated PTEC preserved the expression of molecules typical of fully differentiated tubuli such as alkaline phosphatase and aminopeptidase A and re-established the presence of the endocytic receptor megalin, a phenomenon likely responsible for the maintained ability of these cells to internalize FITC-labeled albumin. The expression of the endocytic receptor megalin by MV-treated PTEC was studied by immunofluorescence, by comparing megalin expression in the presence of 5 µg/ml cisplatin or 5 µg/ml cisplatin+10 µg/ml MVs. Magnification ×100. Nuclei were counterstained with 0.5 mg/ml Hoechst. Three experiments were performed with similar results.

Figure 14:
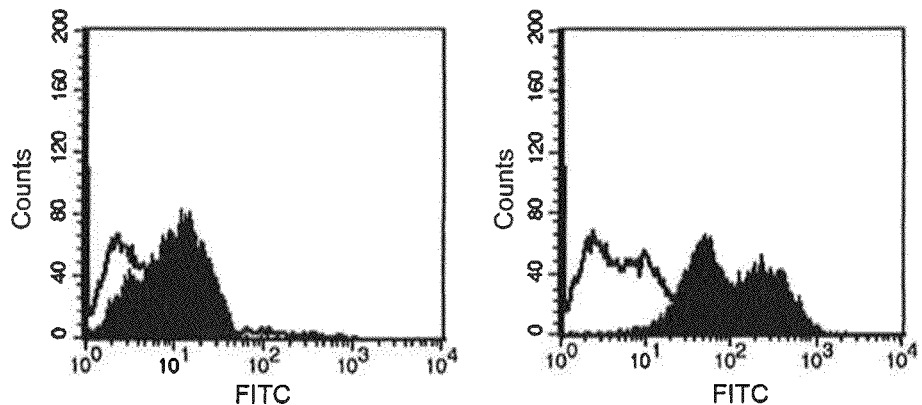
FIG. 14 graphically represents the effect of MVS on the internalization of FITC-albumin by PTECs.

FIG. 14 shows the effect of MVs on the internalization of FITC-albumin by PTECs. Protein uptake was studied after incubation of PTEC monolayers with 50 mg/ml of FITC-conjugated human albumin at 37° C. for 2 h. After FITC-albumin challenge, PTEC were extensively washed 3× with ice-cold PBS and analysed by FACS. Dark curves showed the internalization of albumin in respect to control (open curves). A shows FITC-albumin uptake by 5 µg/ml cisplatin-treated PTEC; B shows FITC-albumin uptake by 5 µg/ml cisplatin-treated PTEC stimulated with 10 µg/ml MVs. Kolomogorov Smirnov statistical analysis was performed. Three different experiments were performed with similar results.

MVs Induce Branching Morphogenesis of PTEC Cultured on Matrigel-Coated Plates and Tubulogenesis In Vivo PTECs cultured for 24 h without FCS on Matrigel-coated plates formed cyst-like structures. The addition of 10 µg/ml MVs resulted in branching morphogenesis of PTECs. We injected PTECs subcutaneously into Matrigel plugs in SCID mice. These cells spontaneously formed a low number of tubular-like structures which significantly increased in the presence of 10 µg/ml MVs. By contrast, cisplatin completely inhibited branching morphogenesis triggering apoptosis that was restored by MV-stimulation. The morphogenesis of PTECs cultured on Matrigel-coated plates in the presence or absence of 10 µg/ml MVs was evaluated. After 24 h, unstimulated PTECs formed cyst-like structures, whereas MVs induced scattering and branching morphogenesis. The in vivo tubulogenesis of PTEC subcutaneously injected into Matrigel plugs in SCID mice was also evaluated. Unstimulated cells formed only few tubular-like structures that were significantly increased in presence of 10 µg/ml.

Figure 15:
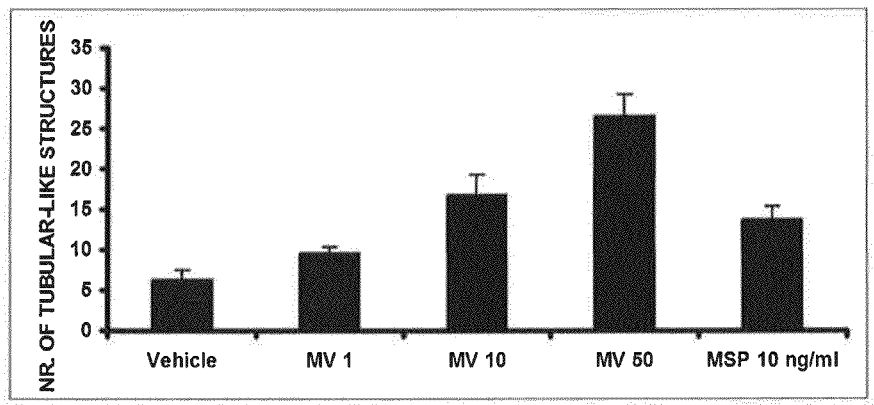
FIG. 15 graphically represents the quantification of MV-induced in vivo tubulogenesis.

The tubulogenic effect of MVs in vivo was dose-dependent. FIG. 15 shows the quantification of MV-induced in vivo tubulogenesis. Count of tubular-like structures was performed in 10 non sequential Matrigel sections (×100 magnification) of PTEC treated with different doses of MVs and injected subcutaneously in SCID mice. Mice were sacrificed after 7 days and Matrigel plugs were observed by fluorescence microscopy. Data are expressed as average number of tubular-like structures/field (magnification ×100) counted in three different experiments. Macrophage Stimulation Protein (MSP 10 ng/ml), a trophic factor for PTEC, was used as the positive control.

Decreased Adhesion of Lymphocytes to PTEC Monolayers

Cytokine-treated PTEC enhanced lymphocyte adhesion, mimicking the inflammatory reaction occurring in vivo in the course of ARF. The addition of MVs to PTEC stimulated with cytokines significantly inhibited lymphocyte adhesion to PTEC, suggesting an anti-inflammatory action of MVs.

Figure 16:
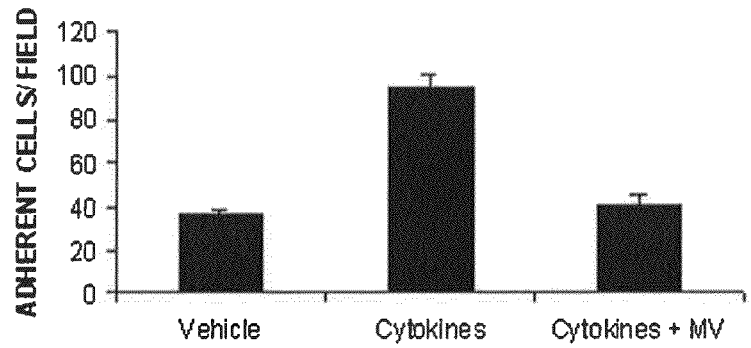
FIG. 16 graphically represents the results of PTEC monolayers incubated for with vehicle alone or inflammatory cytokines in the presence or absence of MVS.

FIG. 16: PTEC monolayers were incubated for 6 h with vehicle alone or inflammatory cytokines (20 ng/ml TNF-alpha and 20 ng/ml IFN-gamma) in the presence or absence of 10 µg/ml MVs. After extensive washing of PTEC monolayer $1 \times 10^4$ PKH2-labeled human lymphocytes were added and incubated in condition of slight agitation for 1 h at 37° C. Non-adherent cells were removed by three washes by PBS and adherent cells were counted by fluorescence microscopy at ×100 magnification and expressed as number of cells/field. Data are means±SD of three different experiments.

MVs Derived from EPC are Able to Induce Cell Proliferation and In Vitro Angiogenesis of Glomerular Endothelial Cells (GECs).

Figure 17:
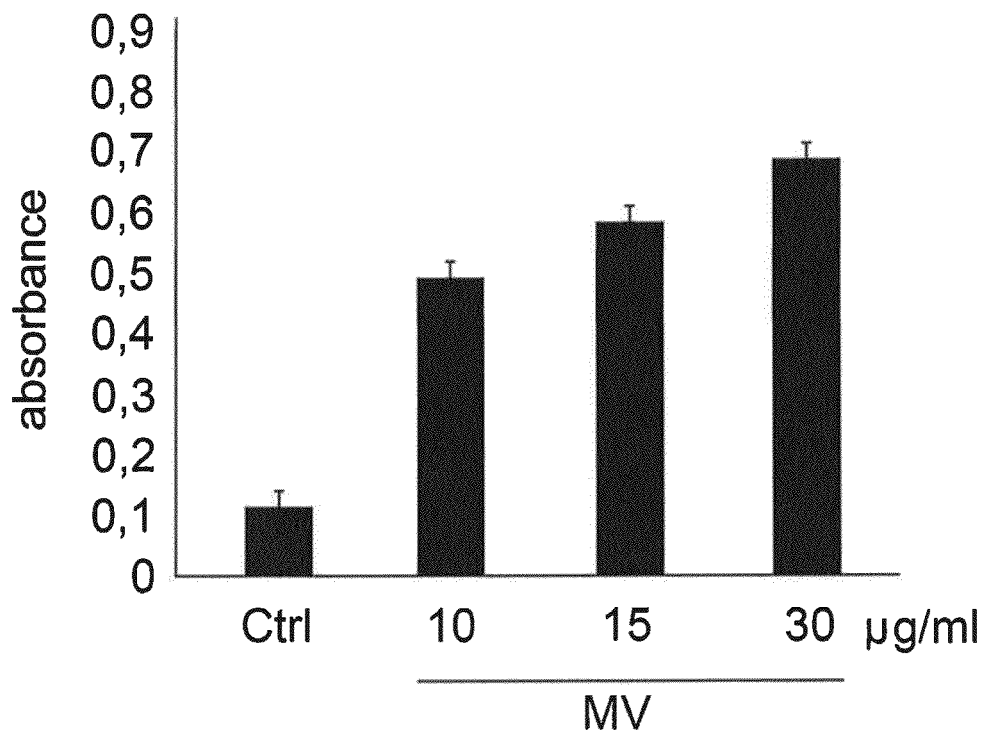
FIG. 17 graphically represents the results of GEC incubated in DMEM with vehicle alone or with different doses of MV.

MV derived from EPC were able to induce cell proliferation and in vitro angiogenesis of glomerular endothelial cells (GEC). Incubation for 48 hours of GEC with different doses of MV (10, 15 and 30 μg/ml) derived from EPC significantly promoted cell proliferation of GEC, in respect to control. As shown in FIG. 17, GEC (8000 cells/well into 96-well plates) were added with 10 μM BrdU, incubated in DMEM with vehicle alone or with different doses of MV. Cells were then fixed with 0.5 M ethanol/HCl and incubated with nuclease to digest the DNA. BrdU incorporated into the DNA was detected using an anti-BrdU peroxidase-conjugated mAb and visualized with a soluble chromogenic substrate. Optical density was measured with an ELISA reader at 405 nm. Results are expressed as mean±ISD of 3 experiments.

In addition different doses of MV (10, 15 and 30 μg/ml) induced in vitro angiogenesis in GEC incubated for 6 hours on Matrigel.

In Vivo Biological Effects of MVs on Renal Repair MVs Promote Regeneration of Experimentally-Induced Acute Tubular Injury To determine whether MVs derived from MSCs from adult bone marrow of C57/BL6 mice were capable of promoting the recovery from acute renal injury, we induced ARF in female C57/BL6 mice with an intramuscular injection of hypertonic glycerol. Glycerol induced myolysis and haemolysis thereby exposing tissues, especially the kidney, to large amounts of myoglobin and haemoglobin. In this murine model, renal function, as measured by serum creatinine and BUN, is impaired between 1-4 days after glycerol administration. In our setting, intra-muscle injection of 7.5 ml/kg glycerol induced significant increases in serum creatinine and BUN, which peaked at day 3, declined at day 10, and normalized at day 21. Intravenous injection of MV-derived from MSC or 1×106 MSCs on day three after receiving glycerol significantly reduced serum creatinine and BUN at days 5 with respect to glycerol-treated mice which were given saline (FIG. 18 and FIG. 19).

Figure 18:
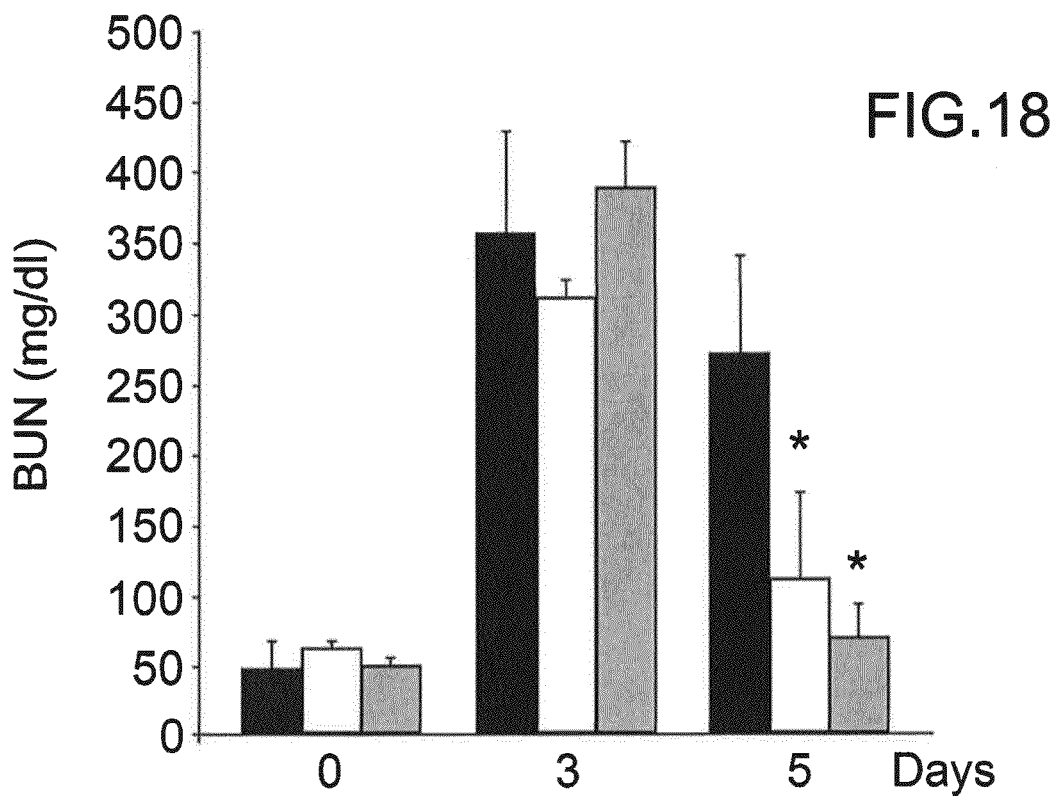
FIG. 18 graphically shows that MVS protected glycerol-treated mice from renal function deterioration.
Figure 19:
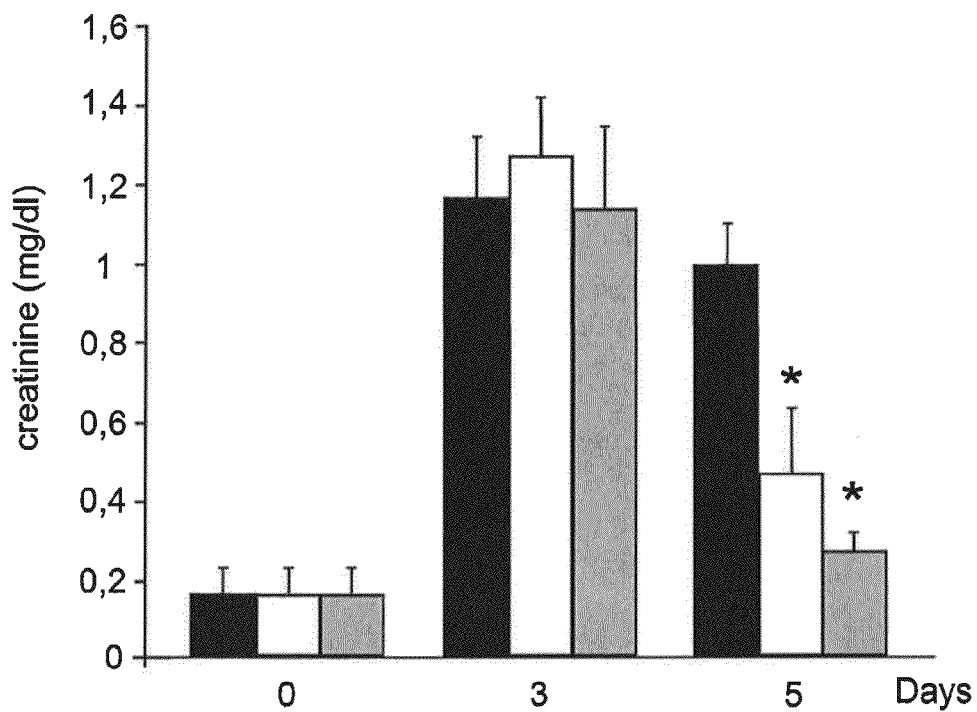
FIG. 19 graphically represents the evaluation of creatinine in mice with glycerol-induced ARF.

FIG. 18 shows that MVs protected glycerol-treated mice from renal function deterioration. Evaluation of Blood Urea nitrogen (BUN) in mice with glycerol-induced ARF untreated (dark column) or treated at day three with 6 μg MVs (white columns) or 1×106 MSC (shaded columns). Data are expressed as mean±SD of three individual experiments and ANOVA was performed: *$p<0.05$ FIG. 19 relates to the evaluation of creatinine in mice with glycerol-induced ARF, untreated (dark column) or treated at day three with 6 μg MVs (white columns) or 1×106 MSC (shaded columns). Data are expressed as mean±SD of three individual experiments and ANOVA was performed: *$p<0.05$ Marked tubular epithelial injury was evident at day 5 in mice with glycerol-induced ARF. The morphological alterations observed in mice with glycerol-induced ARF included vacuolization, loss of brush border and widespread necrosis of tubular epithelial cells and tubular hyaline cast formation. When MVs were injected in glycerol treated mice the tubular lesions were less severe with aspects of tubular regeneration and tubes re-expressed a brush border.

MVs Promote Regeneration of Experimentally-Induced Glomerular Injury

To determine whether MV derived from human EPC were able to induce glomerular regeneration, we used the Thy-1 model of glomerulonephritis which is characterized an acute antibody-mediated glomerular injury: In this model ant-Thy-1 antibodies induce mesangiolysis with loss of glomerular capillaries and accumulation of inflammatory cells. Glomerular injury is associated with proteinuria. Glomerulonephritis (GN) was induced by i.v. administration at day 0 of 250 μg/100 g weight of anti-Thy1-1 antibody (Ab) into femoral vein of 6-wk-old female Lewis rats. Control animals received the same volume of saline injection instead of anti-Thy1.1 Ab. At day 2 when proteinuria was already detectable, 30 μg of EPC-derived MV were injected in the controlateral femoral vein. Control animals received injection of the same amount of vehicle alone (M199 medium Hepes modified plus 1% DMSO). Proteinuria, serum and urine creatinine/urea (24 hour urine collection) were evaluated daily. Mice were sacrificed at the following days D4, D7, D14. Each experimental group included 9 rats.

Figure 20:
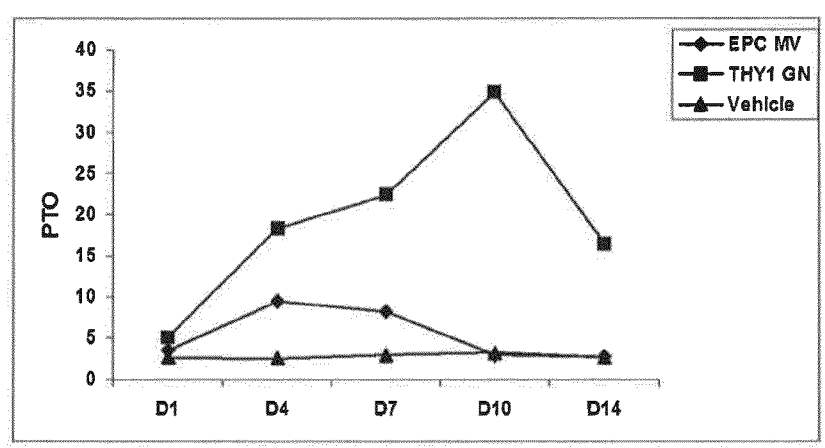
FIG. 20 graphically shows that the administration of MV significantly reduced proteinuria in rats with Thy-1 GN.

As shown in FIG. 20 the administration of MV significantly reduced proteinuria in rats with Thy-1 GN. The histological analysis showed that in rats with Thy-1 GN was present a diffuse injury of capillary walls with microaneurismatic formation and presence of inflammatory cells. The loss of glomerular capillaries was also indicated by the reduced staining for RECA antigen which is an endothelial marker. In addition a diffuse injury of proximal and distal tubules with protein casts within tubule lumen was observed. The histological examination of the kidneys of rats treated with MV demonstrated a reduced glomerular and tubular injury at day 4 and a regeneration of glomerular capillaries as detected of normal distribution of RECA antigen and of tubular cell brush border at day 7.

The inhibition of capillary injury by MV treatment was confirmed by electron microscopy that demonstrated the presence of intact endothelial cell layer and normal distribution of podocytes foot processes in MV-treated rats. In contrast, in rats not treated with MV swelling and detachment of endothelial cells with aspects of phagocytosis of injured endothelium by inflammatory cells was observed. In addition, effacement of foot processes was present.

In conclusion, treatment of Thy-1 GN with MV inhibited proteinuria, glomerular inflammatory lesions and promoted glomerular capillary regeneration and recovery.

CONCLUSIONS

The experimental results obtained suggest that MVs derived from stem cells of different origins, such as endothelial progenitors, mesenchymal, hepatic and renal stem cells, are able to transfer biological signals to renal mature cells, resulting in the de-differentiation of the target cells that acquire an immature phenotype together with the resistance to apoptotic stimuli and migratory and proliferative abilities. The dedifferentiation of resident cells, their migration and proliferation is a key requirement for reparative events following renal tubular and glomerular injury. Actually, the treatment of experimental acute tubular necrosis and of antibody-mediated glomerular injury resulted in an accelerated functional and morphological recovery. Therefore, MVs derived from stem cells may be proposed for re-generative therapy in different renal tubular and glomerular pathological conditions. An advantage of the use of MVs rather than stem cells is the avoidance of the potential tumorigenic effects of stem cells, the avoidance of the need of immunosuppression and the possibility of an unlimited in vitro production.

REFERENCES

1. Bonventre J V, Weinberg J M. Recent advances in the pathophysiology of ischemic acute renal failure. J Am Soc Nephrol. 2003 August; 14(8):2199-210.
2. Bonventre J V. Dedifferentiation and proliferation of surviving epithelial cells in acute renal failure. J Am Soc Nephrol. 2003 June; 14 Suppl 1:S55-61.
3. Iruela-Arispe L, Gordon K, Hugo C, Duijvestijn A M, Claffey K P, Reilly M, Couser W G, Alpers C E, Johnson R J. Participation of glomerular endothelial cells in the capillary repair of glomerulonephritis. Am J Pathol. 1995 December; 147(6):1715-27.
4. Herrera M B, Bussolati B, Bruno S, Morando L, Mauriello-Romanazzi G, Sanavio F, Stamenkovic I, Biancone L, Camussi G. Exogenous mesenchymal stem cells localize to the kidney by means of CD44 following acute tubular injury. Kidney Int. 2007 August; 72(4):430-41.
5. Biancone L, Cantaluppi V, Duo D, Deregibus M C, Torre C, Camussi G. Role of L-selectin in the vascular homing of peripheral blood-derived endothelial progenitor cells. J Immunol, 2004 Oct. 15; 173(8):5268-74.
6. Kunter U, Rong S, Boor P, Eitner F, Muller-Newen G, Djuric Z, van Roeyen C R, Konieczny A, Ostendorf T, Villa L, Milovanceva-Popovska M, Kerjaschki D, Floege J. Mesenchymal stem cells prevent progressive experimental renal failure but maldifferentiate into glomerular adipocytes. J Am Soc Nephrol. 2007 June; 18(6):1754-64.
7. Deregibus M C, Cantaluppi V, Calogero R, Iolacono M, Tetta C, Biancone L, Bruno S, Bussolati B, Camussi G. Endothelial progenitor cell-derived microvesicles activate an angiogenic program in endothelial cells by an horizontal transfer of mRNA. Blood 2007, 110:2440-2448.
8. Chertow G M, Soroko S H, Paganini E P, Cho K C, Himmelfarb J, Ikizler T A, Metha R L. Mortality after acute renal failure: models for prognostic stratification and risk adjustment. Kidney Int. 2006; 70:1120-1126.
9. Metha R L, Pascual M T, Soroko S, Savage B R, Himmelfarb Ikizler T A, Paganini E P, Chertow G M. Program to Improve Care in Acute Renal Disease. Spectrum of acute renal failure in the intensive care unit: the PICARD experience. Kidney Int. 2004; 66:1613-1621.
10. Bonegio R, Lieberthal W. Role of apoptosis in the pathogenesis of acute renal failure. Curr Opin Nephrol Hypertens. 2002; 11:301-308.
11. Tonelli M, Manns B, Feller-Kopman D. Acute renal failure in the intensive care unit: a systematic review of the impact of dialytic modality on mortality and renal recovery. Am J Kidney Dis. 2002 November; 40(5):875-85.
12. Bussolati B, Bruno S, Grange C, Buttiglieri S, Deregibus M C, Cantino D, Camussi G. Isolation of renal progenitor cells from adult human kidney. Am Pathol. 2005 February; 166(2):545-55.
13. Nangaku M. Chronic hypoxia and tubulointerstitial injury; a final common pathway to end-stage renal failure. J Am Soc Nephrol. 2006 January; 17(1):17-25.
14. Herrera M B, Bussolati B, Bruno S, Fonsato V, Mauriello Romanazzi G, Camussi G. Mesenchymal stem cells contribute to the renal repair of acute tubular epithelial injury. Int J Mol Med 2004; 14:1035-1041.
15. Conaldi P G, Biancone L, Bottelli A, Wade-Evans A, Racusen L C, Boccellino M, Orlandi V, Serra C, Camussi G, Toniolo A. HIV-1 kills renal tubular epithelial cells in vitro by triggering an apoptotic pathway involving caspase activation and Fas upregulation. J Clin Invest. 1998 Dec. 15; 102(12):2041-9.
16. Molitoris B A, Sutton T A. Endothelial injury and dysfunction: role in the extension phase of acute renal failure. Kidney Int. 2004 August; 66(2):496-9.

The invention claimed is:
1. A method of inhibiting apoptosis induced by a cytostatic agent comprising administering to a patient in need thereof an effective amount of microvesicles (Mvs) derived from adult human liver stem cells (HLSC).
2. The method according to claim 1, wherein the patient is undergoing chemotherapeutic treatment.
3. The method according to claim 1, wherein the patient in undergoing chemotherapeutic treatment of cancer.
4. The method according to claim 2, for reducing side effects of the chemotherapeutic treatment.
5. The method according to claim 1, wherein the cytostatic agent is selected from the group consisting of Paclitaxel, Lenalidomide, Pomalidomide, Epirubicin, 5Fu, Sunitinib, Lapatinib, Canertinib, cyclophamide, doxorubicin, Lenalidomiden/Dexamethason, Pomalidomide/Dexamethasone, Carboplatin, mitoxantron, oxaliplatin, docetaxel, vinorelbin and combinations thereof.
6. The method according to claim 1, wherein the administering is by intravenous injection.
7. The method according to claim 1, wherein the effective amount is 30 µg/kg to 120 µg/kg body weight.

* * * * *